(12) United States Patent
Sugiura et al.

(10) Patent No.: US 9,234,983 B2
(45) Date of Patent: Jan. 12, 2016

(54) RAIN SENSOR

(71) Applicant: DENSO CORPORATION, Kariya, Aichi-pref. (JP)

(72) Inventors: Makiko Sugiura, Hekinan (JP); Yasuaki Makino, Okazaki (JP); Junichi Ishikawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/375,511

(22) PCT Filed: Mar. 25, 2013

(86) PCT No.: PCT/JP2013/001986
§ 371 (c)(1),
(2) Date: Jul. 30, 2014

(87) PCT Pub. No.: WO2013/145681
PCT Pub. Date: Oct. 3, 2013

(65) Prior Publication Data
US 2015/0036143 A1 Feb. 5, 2015

(30) Foreign Application Priority Data
Mar. 28, 2012 (JP) .................................. 2012-74380

(51) Int. Cl.
*G01N 21/55* (2014.01)
*G01W 1/14* (2006.01)
*B60S 1/08* (2006.01)

(52) U.S. Cl.
CPC ................ *G01W 1/14* (2013.01); *B60S 1/0837* (2013.01); *G01N 21/55* (2013.01); *G01N 2201/062* (2013.01)

(58) Field of Classification Search
CPC ................ G02B 2027/0118; G02B 2027/012; G02B 6/00; G02B 5/32; G01N 21/552; G01N 21/55; G01N 21/35; G01N 21/3554; G01N 21/4738; G01N 2201/0625; G01N 27/226; G01N 2021/435; G01N 2201/0216
See application file for complete search history.

(56) References Cited

U.S. PATENT DOCUMENTS 4,960,996 A * 10/1990 Hochstein ..................... 250/349
4,973,844 A * 11/1990 O'Farrell et al. .......... 250/341.7

(Continued)

FOREIGN PATENT DOCUMENTS

JP 2002-257947 A 9/2002
JP 2006-084353 A 3/2006
JP 2008-275390 A 11/2008

OTHER PUBLICATIONS

International Search Report and Written Opinion of the International Searching Authority mailed Jun. 18, 2013 for the corresponding international application No. PCT/JP2013/001986 (and English translation).

*Primary Examiner* — Michael P Stafira
(74) *Attorney, Agent, or Firm* — Posz Law Group, PLC

(57) ABSTRACT

A rain sensor equipped to a transparent substrate includes a light emitter emitting irradiation lights toward the transparent substrate, light receivers receiving reflected lights of the irradiation lights being reflected on the transparent substrate, a defining section defining an incident angle of each reflected light with respect to each light receiver, and a detection section detecting rainfall amount based on signals output from the light receivers. The light emitter emits the irradiation lights toward an irradiation region defined on the transparent substrate. The irradiation region is divided into multiple detection regions. The detection regions correspond to respective light receivers. The defining section defines the incident angle of each reflected light reflected on the detection region such that each reflected light enters corresponding light receiver. The detection section detects the rainfall amount based on the signals output from the light receivers corresponding to the irradiation regions.

17 Claims, 5 Drawing Sheets

(56) References Cited

U.S. PATENT DOCUMENTS

| | | |
|---|---|---|
| 6,802,631 B1 | 10/2004 | Hog et al. |
| 7,034,932 B2 * | 4/2006 | Kobayashi et al. ........ 356/239.8 |
| 2003/0156291 A1 * | 8/2003 | Tsunetomo et al. .......... 356/445 |
| 2006/0006318 A1 | 1/2006 | Ishikawa et al. |
| 2006/0043322 A1 | 3/2006 | Ishikawa |
| 2006/0163458 A1 | 7/2006 | Reime |
| 2008/0116379 A1 * | 5/2008 | Teder ........................ 250/341.1 |
| 2010/0208060 A1 | 8/2010 | Kobayashi et al. |
| 2013/0037700 A1 | 2/2013 | Michiyama et al. |

* cited by examiner

RAIN SENSOR

CROSS REFERENCE TO RELATED APPLICATION

The present disclosure is a U.S. national stage application of PCT/JP2013/001986 filed on Mar. 25, 2013 and is based on Japanese Patent Application No. 2012-074380 filed on Mar. 28, 2012, the disclosures of which are incorporated herein by reference.

TECHNICAL FIELD

The present disclosure relates to a rain sensor equipped to a transparent substrate.

BACKGROUND ART

Conventionally, as shown in patent literature 1, a raindrop detection apparatus includes a light emitter that emits lights toward an inner wall of a windshield and a light receiver that measures the lights emitted from the light emitter and reflected by the windshield. The raindrop detection apparatus detects an amount of the raindrops landed on an outer wall of the windshield based on an amount of the lights received by the light receiver.

As described above, the light emitter emits the lights toward an irradiation region on the inner wall of the windshield. However, when the irradiation region on the inner wall of the windshield is increased in order to increase a detection range of the raindrops, a ratio of the raindrops attached to the windshield within the irradiation region to the irradiation region decreases. A detection amount of the raindrops is proportional to an area of the raindrops attached to the windshield within the irradiation region. Thus, a detection accuracy of the raindrops may be degraded. The raindrop detection apparatus disclosed in patent literature 1 includes one light receiver with respect to one light emitter. Thus, one light receiver corresponds to one irradiation region (detection region). Thus, when the irradiation region is broadened, the detection accuracy of the raindrops may be degraded.

PRIOR ART LITERATURES

Patent Literature

[Patent Literature 1] JP 4241553 B2

SUMMARY OF INVENTION

In view of the foregoing difficulties, it is an object of the present disclosure to provide a rain sensor that restricts a degradation of a detection accuracy of raindrops.

According to a first aspect of the present disclosure, a rain sensor equipped to a transparent substrate includes a light emitter emitting irradiation lights toward the transparent substrate, a plurality of light receivers receiving reflected lights of the irradiation lights, the reflected lights being reflected on the transparent substrate, a defining section defining an incident angle of each of the reflected lights with respect to each of the light receivers, and a detection section detecting an amount of a rainfall based on signals output from the light receivers. The light emitter emits the irradiation lights toward an irradiation region defined on the transparent substrate. The irradiation region is divided into a plurality of detection regions. The detection regions correspond to respective light receivers. The defining section defines the incident angle of each of the reflected lights reflected on corresponding one of the detection regions such that each of the reflected lights enters corresponding one of the light receivers. The detection section detects the amount of the rainfall based on the signals output from the light receivers corresponding to the irradiation regions.

In the above rain sensor, the irradiation region is divided in to multiple detection regions, and one detection region corresponds to one light receiver. That is, one irradiation region IR corresponds to multiple light receivers. With this configuration, even when the irradiation region IR of the irradiation lights is broadened, a degradation of a raindrop detection accuracy of each light receiver is restricted compared with a configuration in which one irradiation region corresponds to one light receiver. Further, the amount of the rainfall is detected based on the signals output from multiple light receivers that correspond to one irradiation region. With this configuration, a degradation of the raindrop detection accuracy of one light receiver is restricted. Thus, compared with a configuration in which one irradiation region corresponds to one light receiver, a degradation of rainfall amount detection accuracy is restricted.

BRIEF DESCRIPTION OF DRAWINGS

The above and other objects, features and advantages of the present invention will become more apparent from the following detailed description made with reference to the accompanying drawings. In the drawings.

EMBODIMENTS FOR CARRYING OUT INVENTION

The following will describe embodiments of the present disclosure in a case where a rain sensor is attached to a windshield of a vehicle with reference to the drawings. The windshield is also referred to as a transparent substrate.

First Embodiment

Figure 1:
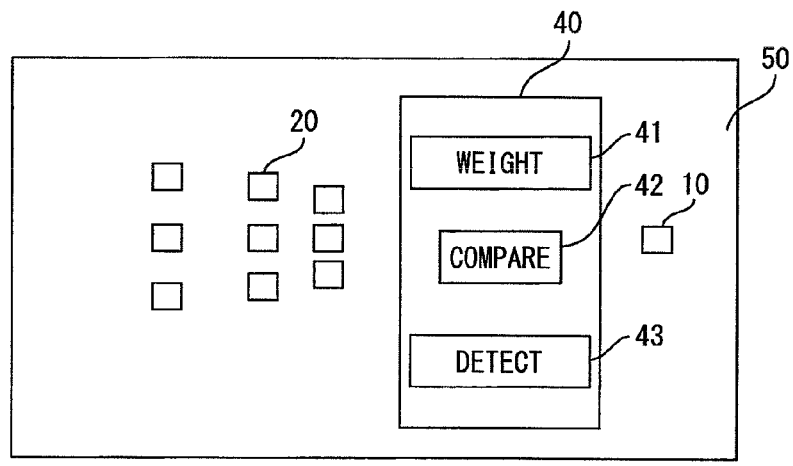
FIG. 1 is a plan view showing a configuration of a rain sensor according to a first embodiment of the present disclosure.
Figure 2:
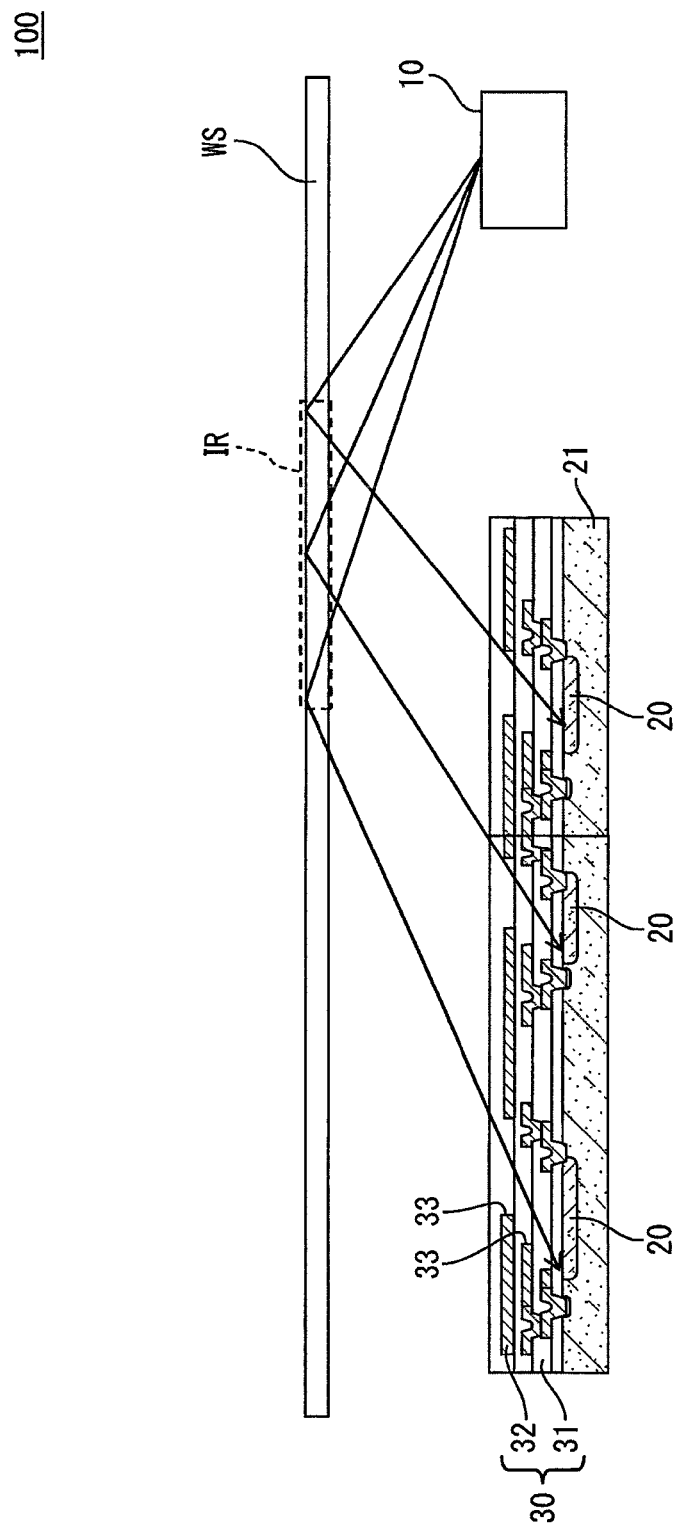
FIG. 2 is a cross sectional view showing a schematic configuration of the rain sensor.
Figure 3:
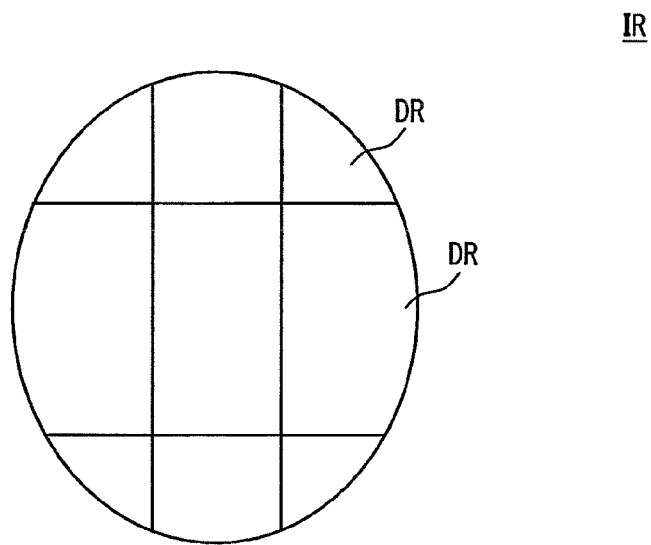
FIG. 3 is a schematic diagram showing an irradiation region and detection regions.

A rain sensor 100 according to the present embodiment will be described with reference to FIG. 1 to FIG. 3. In FIG. 1, a defining section 30, which will be described later, is omitted. In FIG. 2, a detection section 40, which will be described later, is omitted.

The rain sensor 100, mainly, includes a light emitter 10, a light receiver 20, the defining section 30, and the detection section 40. The light emitter 10 emits irradiation lights toward the windshield WS. Among the reflected lights that are emitted from the light emitter 10 and reflected on the windshield WS, the light receiver 20 receives a part of the reflected lights having incident angles equal to incident angles defined by the defining section 30. The light receiver 20 converts the received lights to an electrical signal, and outputs the electrical signal to the detection section 40. The detection section 40, based on the electrical signal output from the light receiver 20, detects the amount of the raindrops attached to the windshield WS, that is, an amount of a rainfall.

When a light is incident on a region of the windshield WS to which water is attached, the light does not reflect on a boundary surface between a windshield glass and the water and transmits through the water toward outside. As a result, the amount of lights received by the light receiver 20 is decreased, and an intensity of the electrical signal output from the light receiver 20 and input to the detection section 40 is decreased. Using above-described phenomenon, the amount of the rainfall can be detected based on the increase or decrease of the intensity of the electrical signal output from the light receiver 20. In the present embodiment, the main parts 10 to 40 are disposed on one substrate 50, and the substrate 50 is equipped to an inner surface of the windshield WS by a fixing member (not shown).

The light emitter 10 emits the lights toward the windshield WS. The light emitter 10 is provided by a light-emitting diode (LED), and one light emitter 10 is disposed on one substrate 50. The light emitter 10 emits lights toward a region, which is surrounded by a dashed line in FIG. 2. Hereinafter, the region toward which the lights are emitted is also referred to as an irradiation region IR. In the present embodiment, in order to secure an area of the irradiation region IR, the lights emitted from the light emitter 10 are obliquely incident on the windshield WS.

The light receivers 20 receive the lights emitted from the light emitter 10 and reflected on the windshield WS. The light receiver 20 is provided by a photodiode, and multiple light receivers 20 are disposed on one substrate 50. As shown in FIG. 3, the irradiation region IR is divided into multiple detection regions DR. Multiple light receivers 20 correspond to one irradiation region IR, and one detection region DR corresponds to one light receiver 20. In the present embodiment, nine light receivers 20 are disposed on one substrate 50. Each of the nine light receivers 20 receives the light reflected on the corresponding detection region DR.

As described above, the lights emitted from the light emitter 10 are obliquely incident on the windshield WS. Accordingly, an angle between the incident light on the irradiation region IR and the reflected light reflected on the irradiation region IR becomes close to an obtuse angle. The light emitter 10 is disposed apart from the light receiver 20 by a predetermined distance so that the light receiver 20 receives the reflected fight. The irradiation region IR has a width. The angle between the incident light and the reflected light becomes close to the obtuse angle when the distance between the irradiation region IR and the light emitter 10 increases. Thus, as shown in FIG. 1, multiple light receivers 20 are arranged in a direction moving away from the light emitter 10. The light receivers 20 are arranged so that a distance between adjacent two light receivers 20 in the direction moving away from the light emitter 10 gradually increases in the direction moving away from the light emitter 10.

The defining section 30 defines an incident angle of the light entering the corresponding light receiver 20. As described above, the irradiation region IR is divided into nine detection regions DR. The defining section 30 defines an incident angle of the light so that the light enters the corresponding light receiver 20 after being reflected on one detection region DR. As described above, multiple light receivers 20 are arranged in the direction moving away from the light emitter 10. Thus, the defining section 30 defines the incident angle of each light entering the corresponding light receiver 20 so that the incident angle increases corresponding to the increase of the distance between the corresponding light receiver 20 and the light emitter 10. The detection region DR is mainly defined by the defining section 30. The detection region DR is defined by the windshield WS, the light emitter 10, a position of each light receiver 20, the incident angle of the light on the windshield WS when the light is emitted from the light emitter 10 toward the windshield WS, and the defining section 30.

The defining section 30 includes one or more transmissive film 31 and one or more light shielding film 32. The transmissive film 31 and a light shielding film 32 are successively laminated on a substrate 21 on which the light receiver 20 is disposed. Each light shielding film 32 has one or more opening portions 33, and the light enters the light receiver 20 through each opening portion 33. As shown in FIG. 2, a shape of the opening portion 33 is formed so that the light reflected on the irradiation region IR (hereinafter, referred to as reflected light for simplification) enters the corresponding light receiver 20. More specifically, a hole is defined by the opening portion 33, and the hole is inclined with respect to a direction perpendicular to the substrate 21. Hereinafter, the direction perpendicular to the substrate 21 is referred to as a reference vertical direction. In FIG. 2, the lights emitted from the light emitter 10 are shown by solid arrows. When the distance between the light emitter 10 and the light receiver 20 is increased, the angle between the incident light and the reflected light becomes close to the obtuse angle. Thus, in each light receiver 20, an angle between an axial direction of the hole corresponding to the light receiver 20 and the reference vertical direction increases with an increase of the distance between the light emitter 10 and the light receiver 20. An area of the detection region DR is mainly defined by an area of the opening portion 33.

A reflection angle on the windshield WS is an angle between a normal line that is perpendicular to the inner surface of the windshield WS and a traveling direction of the light reflected on the windshield WS. An incident angle on the light receiver 20 is an angle between a normal line perpendicular to a plane on which the substrate 21 is positioned and the traveling direction of the light that enters the light receiver 20 after being reflected on the windshield WS. In the present embodiment, the reflection angle is equal to the incident angle.

The detection section 40 detects the amount of the rainfall based on the electrical signals output from the light receivers 20. As described above, one irradiation region IR corresponds to multiple light receivers 20. The detection section 40 detects the amount of the rainfall based on the multiple electrical signals output from the multiple light receivers 20. In the present embodiment, as shown in FIG. 1, the detection section 40 is disposed between the light emitter 10 and the light receiver 20.

The detection section 40 according to the present embodiment includes a weighting section (WEIGHT) 41, a comparing section (COMPARE) 42, and a rainfall amount detecting section (DETECT) 43. The weighting section 41 performs a weighting process to the electrical signals output from respective light receivers 20. The comparing section 42 compares the electrical signal to which the weighting process is performed by the weighting section 41 with a threshold voltage Vth. The rainfall amount detecting section 43 detects the amount of the rainfall based on signals output from the comparing section 42.

Since the light emitted from the light emitter 10 does not have a constant shape, a shape of the irradiation region IR is not constant. Thus, in the irradiation region IR that is mainly defined by the defining section 30, as shown in FIG. 3, a shape of the detection region DR corresponding to each light receiver 20 does not have a constant shape. The area of each detection region DR varies from one another. When the area of each detection region DR varies from one another, the area of a region to which the raindrop attaches varies from one another accordingly. Thus, the electrical signal output from the light receiver 20 corresponding to the detection region DR having a large area is less likely to change from the electrical signal output from the light receiver 20 corresponding to the detection region DR having a small area. The weighting section 41 sets a large-area weighting factor greater than a small-area weighting factor. The large-area weighting factor is a weighting factor to be applied to the electrical signal output from the light receiver 20 corresponding to the detection region DR having an area larger than a predetermined value. The small-area weighting factor is a weighting factor to be applied to the electrical signal output from the light receiver 20 corresponding to the detection region DR having an area smaller than the predetermined value. That is, a value of the large-area weighting factor is greater than a value of the small-area weighting factor.

The detection regions DR include a detection region DR to which the water dropped from a roof or the water flipped by a wiper is more likely to attach and a detection region DR to which the water is less likely to attach. Hereinafter, the detection region DR to which the water is more likely to attach is also referred to as a first detection region, and the detection region DR to which the water is less likely to attach is also referred to as detection region. When the water frequently attaches to the detection region DR to which the water is more likely to attach and the electrical signal is not output from the light receiver 20 corresponding to the detection region DR to which the water is more likely to attach, the rainfall amount detecting section 43 may determine that it is raining. The weighting section 41 according to the present embodiment sets a weighting factor to be applied to the electrical signal output from the light receiver 20 corresponding to the detection region DR to which the water is less likely to attach greater than a weighting factor to be applied to the electrical signal output from the light receiver 20 corresponding to the detection region DR to which the water is more likely to attach. Hereinafter, the weighting factor to be applied to the electrical signal output from the light receiver 20 corresponding to the first detection region is also referred to as a first weighting factor, and the weighting factor to be applied to the electrical signal output from the light receiver 20 corresponding to the second detection region is also referred to as a second weighting factor. That is, the first weighting factor is greater than the second weighting factor. More specifically, the weighting section 41 is provided by multiple amplifiers (not shown). The weighting factors described above correspond to amplifying gains of respective amplifiers, and one amplifier is disposed corresponding to one light receiver 20. Hereinafter, each amplifier is also referred to as a sub weighting section.

The comparing section 42 outputs a high-level signal Hi when the electrical signal output from the light receiver 20 is lower than a threshold voltage Vth, and outputs a low-level signal Lo when the electrical signal output from the light receiver 20 is higher than the threshold voltage Vth. A voltage level of the low-level signal Lo is lower than a voltage level of the high-level signal Hi. Specifically, the comparing section 42 is provided by a comparator. Each light receiver 20 is electrically connected with the comparing section 42 via a corresponding sub weighting section 41 and a switch (not shown). The light receivers 20 are electrically connected with the comparing section 42 successively by turning on the switches corresponding to respective light receivers 20. As a result, the high-level signal Hi or the low-level signal Lo is successively output from the comparing section 42 and is input to the rainfall amount detecting section 43.

The rainfall amount detecting section 43 counts a quantity of the high-level signals Hi output from the comparing section 42, and detects the amount of the rainfall based on the counted quantity. The rainfall amount detecting section 43 receives the electrical signals output from nine light receives 20 via the weighting section 41 and the comparing section 42. For example when three or more light receivers 20 output electrical signals having weak voltage levels, among nine signals output from the comparing section 42, three or more signals are the high-level signals Hi. In this case, the rainfall amount detecting section 43 determines the rainfall, and transmits a driving signal instructing a driving of the wiper to a CPU of the vehicle. More specifically, among nine signals output from the comparing section 42, three to five signals are the high-level signals Hi, the rainfall amount detecting section 43 determines that it is raining lightly and transmits a first driving signal to the CPU. Among nine signals output from the comparing section 42, six to eight signals are the high-level signals Hi, the rainfall amount detecting section 43 determines that it is raining normally and transmits a second driving signal to the CPU. Among nine signals output from the comparing section 42, nine signals are the high-level signals Hi, the rainfall amount detecting section 43 determines that it is raining heavily and transmits a third driving signal to the CPU. The first driving signal includes a command for controlling the wiper to operate at a first speed, the second driving signal includes a command for controlling the wiper to operate at a second speed faster than the first speed, the third driving signal includes a command for controlling the wiper to operate at a third speed faster than the second speed. The rainfall amount detecting section 43 is provided by a microcomputer.

The following will describe advantages provided by the rain sensor 100 according to the present embodiment.

As described above, one irradiation region IR is divided into multiple detection regions DR, and one detection region DR corresponds to one light receiver 20. That is, one irradiation region IR corresponds to multiple light receivers 20. With this configuration, even when the irradiation region IR of the irradiation lights is broadened, a degradation of a raindrop detection accuracy of each light receiver 20 is restricted compared with a configuration in which one irradiation region IR corresponds to one light receiver.

In the present embodiment, the amount of the rainfall is detected based on the electrical signals output from multiple light receivers 20 corresponding to one irradiation region IR. As described above, since a degradation of the raindrop detection accuracy of one light receiver 20 is restricted, a degradation of the rainfall amount detection accuracy is restricted accordingly, compared with a configuration in which one irradiation region corresponds to one light receiver.

The detection section 40 includes the comparing section 42 that compares the electrical signal output from the light receiver 20 with the threshold voltage Vth and the rainfall amount detecting section 43 that detects the amount of the rainfall based on the signal output from the comparing section 42.

With this configuration, a case in which micro amount of water is attached to the detection region DR, a determination that it is raining is restricted. Thus, a degradation of the rainfall amount detection accuracy is restricted.

The detection section 40 includes the weighting section 41 that weights the electrical signal output from each light receiver 20. The electrical signal output from each light receiver 20 and weighted by the weighting section 41 is input to the comparing section 42.

As described above, the detection regions DR includes the detection region DR to which the water is more likely to attach and the detection region DR to which the water is less likely to attach. Thus, the weighting factor is appropriately set for each of the detection regions DR in order to restrict a degradation of the rainfall amount detection accuracy.

The weighting section 41 sets the weighting factor to be applied to the electrical signal output from the light receiver 20 corresponding to the detection region DR to which the water is less likely to attach greater than the weighting factor to be applied to the electrical signal output from the light receiver 20 corresponding to the detection region DR to which the water is more likely to attach.

With this configuration, a determination that it is raining caused by the frequent attaching of the water to the detection region DR to which the water is more likely to attach is restricted. Thus, a degradation of the rainfall amount detection accuracy is restricted.

The weighting section 41 sets the weighting factor to be applied to the electrical signal output from the light receiver 20 corresponding to the detection region DR having the large area greater than the weighting factor to be applied to the electrical signal output from the light receiver 20 corresponding to the detection region DR having the small area.

As described above, when the area of the detection region DR corresponding to each light receiver 20 varies from one another, the attaching area of the raindrop within each detection region DR varies, accordingly. Thus, the electrical signal output from the light receiver 20 corresponding to the detection region DR having the large area is lower than the electrical signal output from the light receiver 20 corresponding to the detection region DR having the small area. Thus, as described above, the weighting factor to be applied to the electrical signal output from the light receiver 20 corresponding to the detection region DR having the large area is set greater than the weighting factor to be applied to the electrical signal output from the light receiver 20 corresponding to the detection region DR having the small area in order to restrict a fluctuation in the electrical signals caused by a difference of the areas of the detection regions DR. As a result, a degradation of the rainfall amount detection accuracy is restricted.

The detection section 40 is disposed between the light emitter 10 and the light receiver 20.

As described above, in order to secure the area of the irradiation region IR, the lights emitted from the light emitter 10 is obliquely incident on the windshield WS. Thus, the angle between the light emitted from the light emitter 10 and the light reflected on the irradiation region IR becomes close to the obtuse angle. Thus, a distance needs to be secured between the light emitter 10 and the light receiver 20 so that the reflected light enters the corresponding light receiver 20. Thus, a region between the light receiver 20 and the light emitter 10 is blank. In the present embodiment, the detection section 40 is disposed at the blank region. With this configuration, increase in size of the rain sensor 100 can be restricted compared with a case in which the detection section is disposed at a region other than the blank region.

Modification Example

Figure 4:
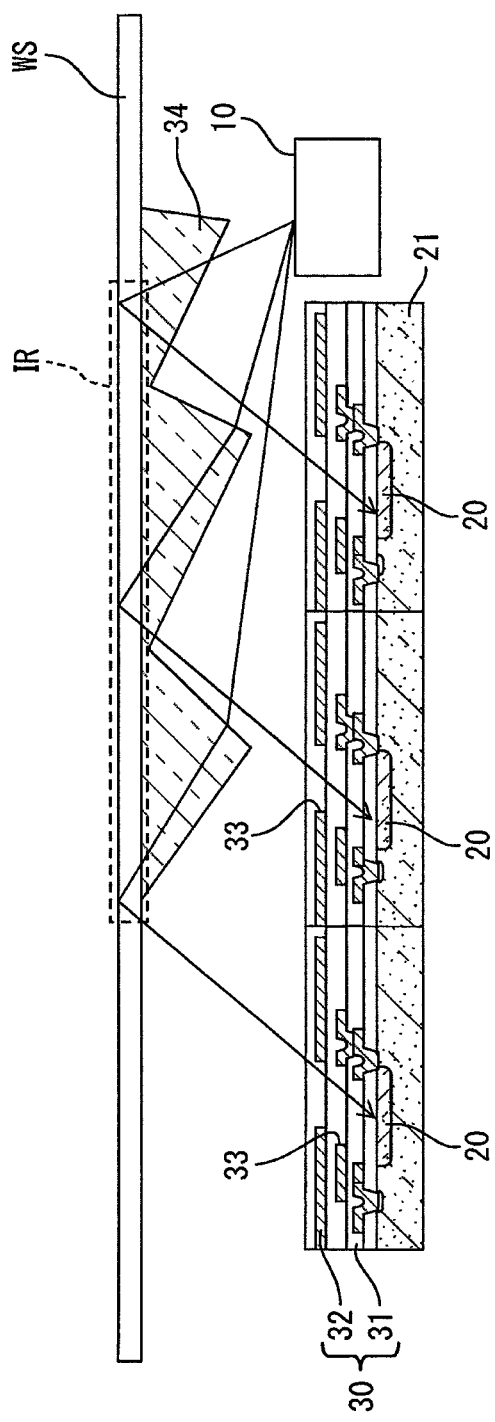
FIG. 4 is a cross sectional view showing a rain sensor according to a modification example.

In the present embodiment, the defining section 30 includes the transmissive film 31 and the light shielding film 32. As another example, as shown in FIG. 4, the defining section 30 may further include a lens 34 that adjusts an incident angle of the light that enters the light receiver 20.

Figure 5:
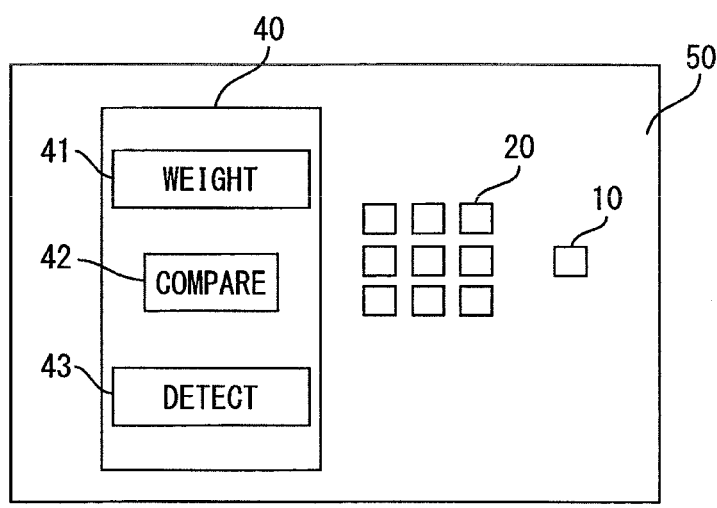
FIG. 5 is a diagram showing a plan view of the rain sensor shown in FIG. 4.

With this configuration, it is no longer necessary to dispose the light emitter 10 apart from the light receiver 20 by a predetermined distance so that the reflected light enters the light receiver 20. Thus, as shown in FIG. 5, a distance between two adjacent light receivers 20 can be set to a constant value.

In the foregoing embodiments, an example in which nine light receivers 20 are disposed on the substrate 50 is described. Further, the number of light receivers 20 is not limited to nine, and may be set to a number equal to or greater than two other than nine.

In the foregoing embodiments, an example in which the irradiation region IR is divided into nine detection regions DR is described. Further, the number of detection regions DR is not limited to nine, and may be set to a different number equal to greater than two.

In the foregoing embodiments, an example in which the detection section 40 includes the weighting section 41 is described. Further, the detection section 40 may not include the weighting section 41.

In the foregoing embodiments, the weighting section 41 sets the weighting factors based on an attaching degree of the water to the detection region DR and the area of the detection region DR. Further, the weighting section 41 may set the weighting factors based on only the attaching degree of the water to the detection region DR. Further, the weighting section 41 may set the weighting factors based on only the area of the detection region DR.

In the foregoing embodiments, the rainfall amount detecting section 43 counts the quantity of the high-level signals Hi output from the comparing section 42, and detects the amount of the rainfall based on the counted quantity of the high-level signals Hi. Further, the rainfall amount detecting section 43 may count the quantity of the low-level signals Lo output from the comparing section 42, and detects the amount of the rainfall based on the counted quantity of the low-level signals Lo.

In the foregoing embodiments, especially, a relationship between the substrate 50 and the substrate 21 is not described. The substrate 50 and the substrate 21 may be provided by the same substrate member, or may be provided by different substrate members.

While the disclosure has been described with reference to preferred embodiments thereof, it is to be understood that the disclosure is not limited to the preferred embodiments and constructions. The disclosure is intended to cover various modification and equivalent arrangements. In addition, while the various combinations and configurations, which are preferred, other combinations and configurations, including more, less or only a single element, are also within the spirit and scope of the disclosure.

The invention claimed is:

1. A rain sensor equipped to a transparent substrate comprising:
   a light emitter emitting irradiation lights toward the transparent substrate;
   a plurality of light receivers receiving reflected lights of the irradiation lights, the reflected lights being reflected on the transparent substrate;
   a defining section defining an incident angle of each of the reflected lights with respect to each of the light receivers; and
   a detection section detecting an amount of a rainfall based on signals output from the light receivers, wherein the light emitter emits the irradiation lights toward an irradiation region defined on the transparent substrate, wherein the irradiation region is divided into a plurality of detection regions, wherein the detection regions correspond to respective light receivers, wherein the defining section defines the incident angle of each of the reflected lights reflected on corresponding one of the detection regions such that each of the reflected lights enters corresponding one of the light receivers, wherein the detection section detects the amount of the rainfall based on the signals output from the light receivers corresponding to the irradiation regions, wherein the detection section includes a weighting section, a comparing section, and a rainfall amount detecting section, wherein the comparing section compares the signal output from each of the light receivers with a threshold voltage, and outputs a high-level signal when the signal output from each of the light receivers is lower than the threshold voltage, wherein the comparing section compares the signal output from each of the light receivers with the threshold voltage, and outputs a low-level signal when the signal output from each of the light receivers is higher than the threshold voltage, a voltage level of the low-level signal is lower than a voltage level of the high-level signal, wherein the rainfall amount detecting section counts a quantity of the high-level signals or a quantity of the low-level signals, and detects the amount of the rainfall based on the quantity of the high-level signals or the quantity of the low-level signals, wherein the weighting section weights the signal output from each of the light receivers, and wherein the comparing section receives the signal output from each of the light receivers and weighted by the weighting section.

2. The rain sensor according to claim 1, wherein the detection regions include at least one first detection region to which water is less likely to attach and at least one second detection region to which the water is more likely to attach, wherein the weighting section applies a first weighting factor to the signal output from one of the light receivers corresponding to the at least one first detection region, wherein the weighting section applies a second weighting factor to the signal output from one of the light receivers corresponding to the at least one second detection region, and wherein the first weighting factor is greater than the second weighting factor.

3. The rain sensor according to claim 1, wherein the detection regions include at least one large-area detection region having an area greater than a predetermined value and at least one small-area detection region having an area smaller than the predetermined value, wherein the weighting section applies a large-area weighting factor to the signal output from one of the light receivers corresponding to the at least one large-area detection region, wherein the weighting section applies a small-area weighting factor to the signal output from one of the light receivers corresponding to the at least one small-area detection region, and wherein the large-area weighting factor is greater than the small-area weighting factor.

4. The rain sensor according to claim 1, wherein the light receivers are arranged in a direction moving away from the light emitter, wherein a distance between adjacent two of the light receivers increases in the direction moving away from the light emitter, and wherein the defining section defines the incident angle of each of the reflected lights with respect to corresponding one of the light receivers such that the incident angle of each of the reflected lights increases in the direction moving away from the light emitter.

5. The rain sensor according to claim 4, wherein the detection section is disposed between the light emitter and the light receivers.

6. The rain sensor according to claim 1, wherein the defining section includes light shielding films and opening portions defined by the light shielding films, and wherein the incident angle of each of the reflected lights with respect to corresponding one of the light receivers is defined by corresponding one of the opening portions.

7. The rain sensor according to claim 6, wherein the defining section includes a lens that adjusts the incident angle of each of the reflected lights with respect to corresponding one of the light receivers.

8. A rain sensor equipped to a transparent substrate comprising:

a light emitter emitting irradiation lights toward the transparent substrate;

a plurality of light receivers receiving reflected lights of the irradiation lights, the reflected lights being reflected on the transparent substrate;

a defining section defining an incident angle of each of the reflected lights with respect to each of the light receivers; and a detection section detecting an amount of rainfall based on signals output from the light receivers, wherein the light emitter emits the irradiation lights toward an irradiation region defined on the transparent substrate, wherein the irradiation region is divided into a plurality of detection regions, wherein the detection regions correspond to respective light receivers, wherein the defining section defines the incident angle of each of the reflected lights reflected on corresponding one of the detection regions such that each of the reflected lights enters corresponding one of the light receivers, wherein the detection section detects the amount of the rainfall based on the signals output from the light receivers corresponding to the irradiation regions, wherein the light receivers are arranged in a direction moving away from the light emitter, wherein a distance between adjacent light receivers increases in the direction moving away from the light emitter, and wherein the defining section defines the incident angle of each of the reflected lights with respect to corresponding one of the light receivers such that the incident angle of each of the reflected lights increases in the direction moving away from the light emitter.

9. The rain sensor according to claim 8, wherein the detection section is disposed between the light emitter and the light receivers.

10. A rain sensor equipped to a transparent substrate comprising:
- a light emitter emitting irradiation lights toward the transparent substrate;
- a plurality of light receivers receiving reflected lights of the irradiation lights, the reflected lights being reflected on the transparent substrate;
- a defining section defining an incident angle of each of the reflected lights with respect to each of the light receivers; and
- a detection section detecting an amount of a rainfall based on signals output from the light receivers,
- wherein the light emitter emits the irradiation lights toward an irradiation region defined on the transparent substrate,
- wherein the irradiation region is divided into a plurality of detection regions,
- wherein the detection regions correspond to respective light receivers,
- wherein the defining section defines the incident angle of each of the reflected lights reflected on corresponding one of the detection regions such that each of the reflected lights enters corresponding one of the light receivers,
- wherein the detection section detects the amount of the rainfall based on the signals output from the light receivers corresponding to the irradiation regions,
- wherein the defining section includes light shielding films and opening portions defined by the light shielding films, and
- wherein the incident angle of each of the reflected lights with respect to corresponding one of the light receivers is defined by corresponding one of the opening portions.

11. The rain sensor according to claim 10,
wherein the defining section includes a lens that adjusts the incident angle of each of the reflected lights with respect to corresponding one of the light receivers.

12. The rain sensor according to claim 8,
wherein the incident angle is positioned between each of the reflected lights and each of the plurality of light receivers.

13. The rain sensor according to claim 8,
wherein the incident angle is respectively located on each of the plurality of light receivers.

14. The rain sensor according to claim 8,
wherein the incident angle is based on the light reflected onto the plurality of light receivers.

15. The rain sensor according to claim 8,
wherein the distance between each of the plurality of light receivers increases as the plurality of light receivers are positioned farther away from the light emitter.

16. The rain sensor according to claim 15,
wherein the plurality of light receivers includes at least three light receivers.

17. The rain sensor according to claim 8,
wherein the plurality of light receivers includes at least three light receivers.

* * * * *